US006905886B2

(12) United States Patent
Sundaram et al.

(10) Patent No.: US 6,905,886 B2
(45) Date of Patent: *Jun. 14, 2005

(54) PRESERVATIVE SOLUTIONS

(75) Inventors: Lata Sundaram, Laguna Niguel, CA (US); Ann Hoang, Lake Forest, CA (US); Stan Shimizu, Trabuco Canyon, CA (US); Elizabeth R. Umelo-Njaka, Trabuco Canyon, CA (US); Darcy A. Thomas, Lake Forest, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 391 days.

This patent is subject to a terminal disclaimer.

(21) Appl. No.: 10/099,498

(22) Filed: Mar. 13, 2002

(65) Prior Publication Data

US 2002/0160353 A1 Oct. 31, 2002

Related U.S. Application Data

(63) Continuation-in-part of application No. 09/637,649, filed on Aug. 11, 2000, now Pat. No. 6,387,711.

(51) Int. Cl.$^7$ .................... G01N 33/546; G01N 33/533; G01N 33/534

(52) U.S. Cl. ..................... 436/534; 436/15; 436/18; 436/526; 436/545; 436/546; 436/804; 436/817; 436/826

(58) Field of Search .................... 436/18, 817, 534, 436/546, 545, 804, 526, 826, 15, 820

(56) References Cited

U.S. PATENT DOCUMENTS

| | | |
|---|---|---|
| 3,886,132 A | 5/1975 | Brewer et al. |
| 4,508,828 A | 4/1985 | Lindall et al. |
| 4,663,295 A | 5/1987 | Vail et al. |
| 4,788,138 A | 11/1988 | Tung et al. |
| 4,868,154 A | 9/1989 | Gilbard et al. |
| 5,124,318 A | 6/1992 | Gatti et al. |
| 5,149,626 A | 9/1992 | Fleming |
| 5,196,349 A | 3/1993 | Piran et al. |
| 5,208,041 A | 5/1993 | Sindrey |
| 5,496,801 A | 3/1996 | Hothius et al. |
| 5,834,226 A | 11/1998 | Maupin |
| 5,847,086 A | 12/1998 | Farb et al. |
| 5,981,485 A | 11/1999 | O'Conner et al. |

*Primary Examiner*—Mary E. Ceperley
(74) *Attorney, Agent, or Firm*—Stout, Uxa, Buyan & Mullins, LLP; Donald E. Stout; Greg S. Hollrigel

(57) ABSTRACT

This invention relates to preservative solutions for peptides, for example, parathyroid hormone, insulin-like growth factor binding protein 3 (IGFBP3), adrenocorticotropic hormone (ACTH) and mixtures thereof. Preferably, the peptides preserved by the solutions are non-reconstituted. In one embodiment, the preservative solutions comprise a polyvinyl alcohol, EDTA component and molybdic component.

20 Claims, 1 Drawing Sheet

PRESERVATIVE SOLUTIONS

This application is a continuation-in-part of U.S. patent application Ser. No. 09/637,649, filed Aug. 11, 2000, now U.S. Pat. No. 6,387,711, the disclosure of which is incorporated in its entirety herein by reference.

SUMMARY OF THE INVENTION

This invention relates to preservative solutions for peptides, for example, parathyroid hormone, insulin-like growth factor binding protein 3 (IGFBP3), adrenocorticotropic hormone (ACTH) and mixtures thereof. In one embodiment, the peptides of this invention may comprise about 10 to about 500 amino acids. Preferably, the peptides preserved by the solutions are non-reconstituted. Even more preferably, the peptides are substantially preserved in their native conformations. In one embodiment, the preservative solutions comprise a polyvinyl alcohol, EDTA component and molybdic component. In one embodiment, the EDTA component comprises an EDTA and the molybdic component comprises a molybdate.

Further in accordance with the present invention, the solution comprises a non-binding reducer, for example a t-octylphenoxypolyethoxyethanol (TX-100). Still further in accordance with the present invention, the solution comprises a protein component selected from the group consisting of human serum, bovine serum albumin, fish skin gelatin and mixtures thereof. In one embodiment, the preservative solutions have pH's of about 5 to about 8, preferably about 6 to about 7.7.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DESCRIPTION OF THE PREFERRED EMBODIMENTS

Figure 1:
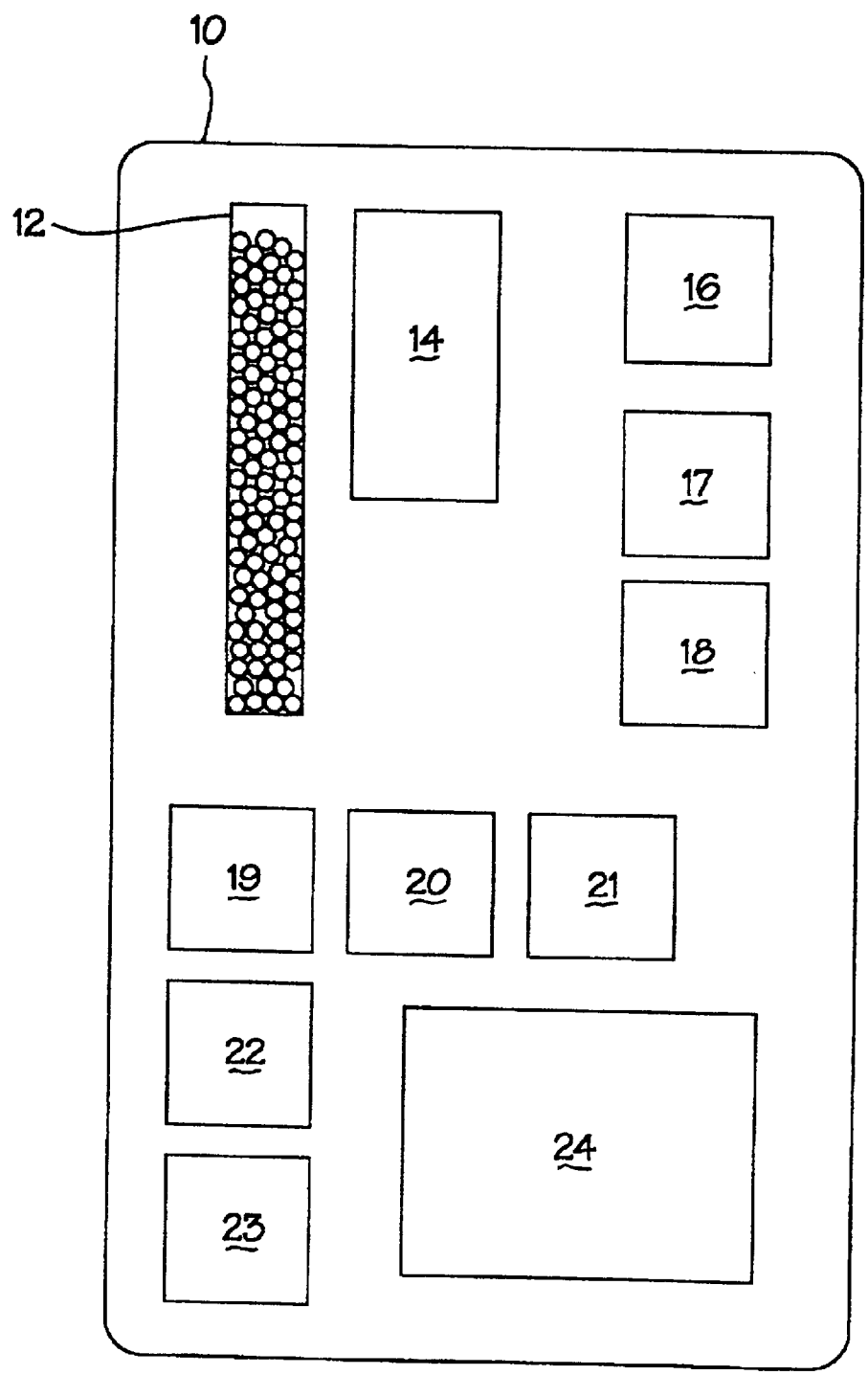
FIG. 1 is a schematic representation of a parathyroid hormone diagnostic kit.

The present invention provides for preservative solutions for peptides. The inventive preservative solutions are effective to preserve non-reconstituted or reconstituted peptides. Preferably, the solutions are effective in preserving non-reconstituted peptides. Reconstituted peptides and non-reconstituted peptides differ in that the reconstituted peptides have been subjected to a lyophilization and/or freeze-dried process, wherein the non-reconstituted peptides have not.

The solutions of the present invention is effective to preserve peptides such as the parathyroid hormone (PTH), insulin-like growth factor binding protein 3 (IGFBP3), adrenocorticotropic hormone (ACTH), the like and mixtures thereof. Non-limiting examples of other peptides which may be preserved by the solutions of the present invention include: insulin, glucagon, somatostatin, pancratic polypeptide, thyroid hormones, antidiuretic hormones (ADH), oxytocin, thyroid stimulating hormone, lutenizing hormone (LH), follicle stimulating hormone, growth hormone, prolactin, gonadotropin releasing hormone, lutenizing hormone releasing hormone, thyrotropin releasing hormone, prolactin inhibiting factor, calcitonin the like and mixtures thereof.

The solutions of the present invention effectively preserve a peptide by keeping the peptide in a stable state in the solution. A peptide is stable when it does not degrade, loose its conformation or become unrecognizable by a detector, for example an antibody, for that peptide. The solutions preserving these peptides are preferably kept in a cool environment. In one embodiment, the solutions are kept at −20 degrees C. to about 10 degrees C., preferably about 2 degrees C. to about 8 degrees C., more preferably at about 4 degrees C. In one embodiment, the solutions of the present invention are effective to keep 100% of the peptides stable for more than about six months, preferably more than about 9 months, even more preferably more than about 12 months. In one embodiment, the solutions of the present invention are effective to keep about 80%, preferably about 90%, of the peptides stable for more than about six months, preferably more than about 9 months, even more preferably more than about 12 months.

Preferably, the preservative solutions are able to preserve peptides at very low concentrations. For example, the concentrations in the solution are about 1 picogram/ml to about 1800 picogram/ml, preferably about 100 picogram/ml to about 1000 picogram/ml.

In a broad embodiment, the preservative solutions comprise a polyvinyl alcohol, EDTA and molybdate. In one embodiment, solutions of this invention comprises about 0.10% to about 1% (% v/v), preferably about 0.5% (% v/v), of a polyvinyl alcohol. The polyvinyl alcohols of this invention preferably have a molecular weight of about 30,000 dalton to about 70,000 dalton. For example, a polyvinyl alcohol purchased from Sigma may be employed in accordance with the present invention.

In one embodiment, the preservative solutions comprise about 0.10% to about 0.50% (% w/v), preferably about 0.17% (% w/v), of an EDTA component. In one embodiment, the EDTA component comprises an EDTA salt, for example EDTA disodium salt. Preferably, the EDTA salt dissolves in the solution.

In one embodiment, the preservative solutions comprise about 0.10% to about 1.00% (% w/v), preferably about 0.7% (% w/v), of a molybdic component. In one embodiment, the molybdic component comprises a molybdenum. In one embodiment, the molybdic component comprises a molybdate salt, for example sodium molybdate. Preferably, the molybdate salt dissolves in the solution.

In one embodiment, the preservative solution further comprises a non-specific binding reducer. Preferably, a non-specific binding reducer is effective to enhance the preserving effect of the solution. In one embodiment, a non-specific binding reducer comprises a detergent, for example a non-ionic detergent. A useful non-ionic detergent for the solutions of this invention includes is t-octylpheoxypolyethoxyethanol sold under the brand name TRITON X-100 by Sigma, St. Louis, Mo. In one embodiment, the solution comprises about 0.1% to about 1.0% (% v/v), preferably about 0.5% (% v/v), of a non-specific binding reducer, for example a t-octylphenoxypolyethoxyethanol (TX-100). Non-limiting examples of other non-ionic detergent include: TW20, Nonidet P10 (NP10), APO-10, Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, Genapol C-100, Genapol X-80, Genapol X-100, Heptane-1,2,3-triol, n-Heptyl-β-D-glucopyranoside, n-Heptyl-β-D-thioglucopyranoside, the like and mixtures thereof.

In one embodiment, the preservative solution further comprises a protein component. A protein component may be selected from a human serum, a bovine serum albumin, protease free bovine serum albumin, fish skin gelatin, the like and mixtures thereof. In one embodiment, the solutions of the present invention comprise about 2.0% (% w/v) of a protein component.

It has been surprisingly discovered that a solution of the present invention comprising a protease free bovine serum albumin is very effective in preserving IGFBP3. For example, a preservative solution which is very effective in preserving IGFBP3, preferably non-reconstituted IGFBP3, comprises about 1.67 mg/ml of dissolved EDTA disodium salt, about 7.2 mg/ml of dissolved sodium molybdate, about 0.225% (% w/v) of fish skin gelatin purchased from Sigma (Gelatin from cold water fish), about 2.50% (% w/v) of protease free bovine serum albumin, and about 0.50% (% v/v) of polyvinyl alcohol, all of which are dissolved in a phosphate saline buffer, for example a 10 mM phosphate saline such as Chemi PBS. Optionally, this particular preservative solution may further comprise about 0.50% (% v/v) of t-octylpheoxypolyethoxyethanol (TRITON X-100). In one embodiment, the pH of this solution is about 7.7. Preferably, the IGFBP3 may be preserved for over six months, more preferably over 9 months, even more preferably over 12 months at about −20 degrees C. to about 8 degrees C.

It has also been surprisingly discovered that a solution comprising an EDTA component, a molybdic component and an acetate buffer may be effective to preserve a peptide, for example an IGFBP3. For example, a preservative solution which is very effective in preserving IGFBP3, preferably non-reconstituted IGFBP3, comprises about 1.67 mg/ml of dissolved EDTA disodium salt, about 7.2 mg/ml of dissolved sodium molybdate, about 0.225% (% w/v) of fish skin gelatin purchased from Sigma (Gelatin from cold water fish), about 2.50% (% w/v) of protease free bovine serum albumin, all of which are dissolved in an acetate buffer, for example a 0.2 M acetate buffer. Optionally, this particular preservative solution may further comprise about 0.50% (% v/v) of t-octylpheoxypolyethoxyethanol (TRITON X-100). In one embodiment, the pH of this solution is about 5 to about 6, for example about 5.4. Preferably, the IGFBP3 may be preserved for over six months, more preferably over 9 months, even more preferably over 12 months at about −20 degrees C. to about 8 degrees C.

In one embodiment, the solutions of the present invention have a pH of about 5.5 to about 8, preferably about 6 to about 7.7. It is surprisingly discovered that a solution of the present invention comprising a pH of about 6 is very effective in preserving an adrenocorticotropic hormone (ACTH). For example, a preservative solution which is very effective in preserving ACTH, preferably non-reconstituted ACTH, has a pH of about 6 and comprises about 1.67 mg/ml of EDTA dissolved disodium salt, about 7.2 mg/ml of sodium molybdate, about 0.225% (% w/v) of Fish skin gelatin purchased from Sigma, about 2.50% (% w/v) of human serum, about 0.50% (% v/v) of t-octylpheoxypolyethoxyethanol (TRITON X-100), and about 0.50% (% v/v) of polyvinyl alcohol, all of which are dissolved in a phosphate saline buffer, for example a 10 mM phosphate saline buffer such as Chemi PBS. Preferably, the ACTH may be preserved for over six months, more preferably over 9 months, even more preferably over 12 months.

The present invention also provides for kits comprising the preserving solutions. These kits may be employed in detecting therapeutic or, preferably, diagnostic concentrations of peptides. Furthermore, these kits may be employed for assaying any peptide by using the appropriate antibodies.

For example, FIG. 1 discloses a diagnostic test kit 10 for performing an assay for an intact parathyroid hormone (PTH). The kit comprises a PTH antibody coated with beads 12, acridinium ester labeled PTH Antibody solution 14, six standards 16–21, two controls 22–23, and saline wash concentrate 24, all of which are stored in appropriate containers. Other kits may have other materials, including more or less standards and controls. In the preferred embodiment of the invention, the kit is used in conjunction with a luminometer, but any suitable spectral reading instrument may be used. Other embodiments, of the invention may have suitable label on the peptide antibody and any suitable instrument for measuring the label, such as radioisotope label and an instrument that reads radioisotope.

The PTH standards 16–21 and controls 22–23 contain PTH in a substantially non-peptide matrix with preservatives. Other embodiments of the invention may use any non-reconstituted PTH or other peptide the diagnostic test kit 10. In preferred embodiments of the invention, the standards 16–21 and the controls 22–23 have a shelf life at 4 degrees C. of at least six months, or more preferably at least nine months, or even preferably at least a year, as a result of the preservatives.

In a preferred embodiment of the invention, the matrix comprises phosphate buffered saline, but other embodiments of the invention may have other solutions, both buffered and non-buffered. In a preferred embodiment of the invention, the preservatives are polyvinyl alcohol, EDTA di-sodium salt, and sodium molybdate. In a more preferred embodiment of the invention, there is less than 1% polyvinyl alcohol, less than 1 % sodium molybdate, and less than 0.5% EDTA di-sodium salt dissolved in the buffer solution. In a highly preferred embodiment of the invention, there is approximately 0.5% polyvinyl alcohol, 0.7% sodium molybdate, and 0.17% EDTA di-sodium salt, dissolved in the buffer solution.

In an embodiment of the invention, a non-specific bonding reducer such as a non-ionic detergent. In a preferred embodiment of the invention, the non-ionic detergent is t-octylpheoxypolyethoxyethanol sold under the brand name TRITON X-100 by Sigma, St. Louis, Mo., is added to the standards 16–21 and controls 22–23 to correct for high non-specific binding of the non-peptide matrix. In a preferred embodiment of the invention, less than 1.5% Triton X-100 is added to the matrix, and in a highly preferred embodiment of the invention, 0.5% Triton X-100 is added to the matrix.

In a preferred embodiment of the invention, the standards 16–21 and the controls 22–23 are made by spiking the matrix with concentrated PTH solution. In a preferred embodiment of the invention, the standards 16–21 are spiked such that the levels of PTH therein are approximately 0, 5, 15, 50, 150 and 500 picograms/mL respectively. Other embodiments of the invention may have more or less standards and the standards may have other percentages of PTH. In an embodiment of the invention, the controls 22–23 have PTH levels within the range of the standards 16–21.

In a more preferred embodiment of the invention, the concentrated PTH solution is made by compounding the PTH into the solution of the matrix. In a more highly preferred embodiment of the invention, the solution comprises the phosphate buffered saline earlier described.

In another embodiment of the invention, the concentrated PTH solution required to make the standards and controls is prepared in the above matrix with preservatives and TX100 along with a very small amount of PTH free human serum. This alternative embodiment results in a relatively low percentage of peptide that is required to reduce the non-specific binding level acceptable for this assay in order to read the low patients correctly. In a preferred embodiment of the invention, the standards and controls are spiked with the concentrated PTH solution such that the standards and controls contain 2% of human serum.

The PTH antibody coated beads 12 are polystyrene beads coated with PTH goat polyclonal antibody. In an embodiment of the invention, there are 100 beads of suitable size. Other embodiments of the invention may use any suitable substrate coated with the PTH antibody. The acridinium ester labeled PTH antibody solution 14 is chemiluminescent labeled PTH goat polyclonal antibody in a buffered protein solution. In an embodiment of the invention, 10 mLs of the solution 14 is provided in the kit 10. In the preferred embodiment of the invention, there is 50 mLs of saline wash concentrate 24.

Other materials needed to perform the test may include, 12×75 mm borosilicate glass tubes, a test tube rack, 100 uL and 200 uL precision pipettors, 100 uL and 500 uL repeating dispenser, a trigger set, luminometer performance controls, reference control sera, bead dispenser capable of dispensing 6 mm beads, distilled or deionized water, timer, mixer, film to cover the tubes, luminometer or other spectral reading instrument, bead washer capable of washing 6mm beads or repeating dispenser capable of delivering 2 mL, and rotator capable of maintaining 180+/−10 rpm. The trigger set is composed of a trigger 1 and a trigger 2. The trigger 1 has 0.1N nitric acid and 0.325% hydrogen peroxide. The trigger 2 has 0.25N sodium hydroxide and 0.125% of a detergent, cetyltrimethylammonium chloride. The acridiunium ester on the acridinium ester labeled PTH antibody solution 14 emits light under alkaline oxidation and trigger the trigger set serves this purpose.

The assay procedure for analyzing a patient sample involves bringing the kit 10 to room temperature. All liquid components of the kit and all samples are mixed by gentle inversion. The saline wash concentrate 24 is diluted appropriately with the distilled or deionized water to have a concentration of 0.9% sodium chloride.

Continuing the assay procedure, the test tubes (not shown) are appropriately labeled. 200 uL of the standards 16–21, the controls 22–23, and the patient sample are delivered directly to the bottom of a respective test tube. 100 uL of antibody solution 14 is added to the bottom of each test tube and v one bead 12 is added to each test tube. In a preferred embodiment of the invention, the bead 12 is added with minimal splashing. In a more preferred embodiment of the invention, the test tube is tilted to enable the bead 12 to gently enter the solution in the test tube.

In a next step of the procedure, the liquid filled test tubes are incubated on the rotator at 180+/−10 rpm's at room temperature for two hours. In a saline wash step of the assay, the beads are washed three times in an automated washing station, using 2 mL of working saline solution, after incubation. In an alternative embodiment of the invention, the beads may be manually washed. The manual washing step comprises aspirating the tubes, adding three mL of saline solution to the tubes, aspirating the tubes, and repeating three more times the adding and aspirating steps.

Next, each bead is counted in the luminometer using Trigger solutions 1 and 2 for two seconds. In a preferred embodiment of the invention, the standards 16–21,the controls 22–23, and the patient samples are assayed in duplicate. The relative light unit read from the luminometer for the duplicates is averaged and used for the reduction of data and calculation of the results using techniques known in the art.

Borosilicate glass test tubes are used in a preferred embodiment of the invention due to their inherently low luminescence background and low non-specific binding characteristics.

Patient samples that are greater than the highest standard 21 are diluted with the zero standard 16 and reassayed with the result being multipled by the dilution factor.

In a preferred embodiment of the invention, the assay should be of serum. Other embodiments of the invention may use EDTA plasma. Duplicate assays require 400 □L of serum. For an more accurate comparison with normal values, a fasting morning serum sample should be obtained. The blood sample is collected in a red-top venipuncture tube (no additives) and allowed to clot. The sample is centrifuged, preferably in a refrigerated centrifuge, and the serum is separated from the cells. The sample should be frozen immediately (−20° C. or below) or stored as outlined below.

| STORAGE CONDITION OF PATIENT'S SERUM | TIME |
| --- | --- |
| At room temperature after collection | 2 hours |
| Refrigerated at 4° C. | 8 hours |
| Frozen at −20° C. | 4 months |
| Frozen at −70° C. | 11 months |

There are other embodiments of the invention that may use the peptides stored with preservatives having an extended shelf life and peptides were not previously freezed dried or otherswise preserved in a manner that requires reconstitution for standards and controls. An example of such an embodiment is an immunoradiometric assay of intact PTH (IRMA of intact PTH). In an IRMA of intact PTH, the standards, control, and samples are incubated with a tracer containing an antibody label using radio isotope idodine 125 and solid phase, such as the above mentioned polysterene beads coated with a PTH antibody. The incubation is performed with the materials being stationary at room temperature for 20 to 24 hours. The solid phase is washed twice with 2.0 mL of working wash solution and counted in a gamma counter for 1 minute. In an embodiment of the invention for the IRMA of the intact PTH, the standards and controls have a buffered human serum matrix.

In another embodiment, the intact PTH diagnostic procedure involves delivering 150 uL of two calibrators, two controls, samples, and 50 uL of assay buffers and 25 uL of acridinium ester labeled antibody solution into a cuvette strip. The strip is transported into an incubator chamber and incubated for 20 minutes at 37 degrees C. After the initial incubation, 25 uL of biotinylated antibody solution and 25 uL of streptavidin coated magnetic particles are added to each well and the incubation is prolonged another 10 minutes. Then, the wells are washed, aspirated with the particles held to the bottom of each well with magnets, triggered, and read in a measuring chamber. This embodiment may have a reagent cartridge that holds all the reagents that go into the reaction such that the procedure may involve an automated pipette machine. In this embodiment, the reagent cartridge and the calibrators/controls may be provided separately as opposed to being in the same kit.

In other embodiments of the invention, other peptides may be kept in a substantially non-protein matrix with preservatives. Still further embodiments of the invention may be kept in a substantially non-protein matrix with preservatives and a non-specific bonding reducer. In other embodiments of the invention, diagnostic test kits may contain peptides kept in the substantially non-protein matrices described herein.

Various U.S. patents, U.S. patent applications and other references have been referred to herein. The disclosures of these patents are incorporated in their entirety herein by reference. The disclosure of Garrity et al. U.S. patent application Ser. No. 09/761,969 is incorporated in its entirety herein by reference.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A solution of a diagnostic system, comprising a non-reconstituted peptide, a polyvinyl alcohol, an EDTA water soluble salt, and a water soluble salt of molybdenum, wherein the peptide remains stable in the solution for at least six months.

2. The solution of claim 1 wherein the EDTA water soluble salt is an EDTA disodium salt, and wherein the water soluble salt of molybdenum is sodium molybdate.

3. The solution of claim 1 wherein the preservative comprises about 0.10% to about 1% (% v/v) polyvinyl alcohol, about 0.10% to about 0.50% (% w/v) of a dissolved EDTA di-sodium salt and about 0.10% to about 1.00% (% w/v) of a dissolved molybdate salt.

4. The solution of claim 1 wherein the preservative comprises about 0.5% (% v/v) polyvinyl alcohol, about 0.17% (% w/v) dissolved EDTA di-sodium salt, and about 0.7% (% w/v) dissolved molybdate salt.

5. The solution of claim 1 further comprising a non-binding reducer.

6. The solution of claim 1 further comprising approximately 0.5% t-octylphenoxypolyethoxyethanol (TX-100).

7. The solution of claim 1 further comprising at least one of bovine serum albumin and fish skin gelatin.

8. The solution of claim 1 further comprising about 2.0% of at least one of bovine serum albumin and fish skin gelatin.

9. The solution of claim 1 having a pH of about 5 to about 8.

10. The solution of claim 1 having a pH of about 6.

11. The solution of claim 1 wherein the peptide is selected from the group consisting of parathyroid hormone, insulin-like growth factor binding protein 3 (IGFBP3), and adrenocorticotropic hormone (ACTH).

12. A diagnostic test system comprising:
   a. a plurality of standards of known percentages of a non-reconstituted peptide in a solution comprising a preservative, wherein the standards have a useful shelf life of at least six months, the preservative comprises a polyvinyl alcohol, an EDTA water soluble salt, and a water soluble salt of molybdenum;
   b. a solid phase coated with anti-peptide antibody; and
   c. a composition of labeled antibody of the peptide.

13. The system of claim 12 wherein the EDTA water soluble salt comprises a dissolved EDTA di-sodium salt and the water soluble salt of molybdenum comprises a dissolved sodium molybdate.

14. The system of claim 12 wherein the preservative comprises about 0.10% to about 1% (% v/v) polyvinyl alcohol, about 0.10% to about 0.50% (% w/v) dissolved EDTA di-sodium salt and about 0.10% to about 1.00% (% w/v) dissolved molybdate.

15. The system of claim 12, wherein the solution further comprises a non-binding reducer.

16. The system of claim 12, wherein the solution further comprises approximately 0.5% t-octylphenoxypolyethoxyethanol (TX-100).

17. The system of claim 12, wherein the solution further comprises a protein selected from the group consisting of bovine serum albumin, and fish skin gelatin.

18. The system of claim 12, wherein the solution has a pH of about 5 to about 8.

19. The system of claim 12, wherein the solution has a pH of about 6.

20. The system of claim 12 wherein the peptide is selected from the group consisting of parathyroid hormone, insulin-like growth factor binding protein 3 (IGFBP3), and adrenocorticotropic hormone (ACTH).

* * * * *

UNITED STATES PATENT AND TRADEMARK OFFICE
CERTIFICATE OF CORRECTION

PATENT NO. : 6,905,886 B2
DATED : June 14, 2005
INVENTOR(S) : Sundaram et al.

It is certified that error appears in the above-identified patent and that said Letters Patent is hereby corrected as shown below:

Column 6,
Line 7, "16-21,the;" should read -- 16-21, the --.

Signed and Sealed this

Twenty-third Day of August, 2005

JON W. DUDAS
*Director of the United States Patent and Trademark Office*